United States Patent [19]
Hance

[11] 3,950,992
[45] Apr. 20, 1976

[54] IMMERSION SAMPLER FOR MOLTEN METAL

[75] Inventor: Richard James Hance, Philadelphia, Pa.

[73] Assignee: Leeds & Northrup Company, North Wales, Pa.

[22] Filed: Aug. 27, 1975

[21] Appl. No.: 608,138

[52] U.S. Cl. ............................ 73/354; 73/425.4 R; 73/DIG. 9
[51] Int. Cl.² ............................................ G01N 1/12
[58] Field of Search ........ 73/425.4 R, 425.6, DIG. 9, 73/354; 249/DIG. 4

[56] References Cited
UNITED STATES PATENTS

| | | | |
|---|---|---|---|
| 3,295,171 | 1/1967 | Strange et al. | 73/DIG. 9 |
| 3,367,189 | 2/1968 | Curry, Jr. | 73/DIG. 9 |
| 3,455,164 | 7/1969 | Boyle | 73/DIG. 9 |
| 3,463,005 | 8/1969 | Hance | 73/DIG. 9 |

*Primary Examiner*—S. Clement Swisher
*Attorney, Agent, or Firm*—Raymond F. MacKay

[57] ABSTRACT

An immersion molten metal sampling device of a type usable to obtain a sample of molten steel from a furnace and to measure the temperature of the molten metal in the furnace. The device includes a high density monolithic ceramic mold capable of obtaining a flat, rectangular shaped sample of the molten metal for spectrographic analysis as well as a pin sample for combustion analysis. The construction of the sampler avoids contamination of the sample by using gas permeable substances that are gaseous inert at the temperature of the molten metal while at the same time eliminating problems due to leakage of the molten metal through vent passages and seams in the mold.

14 Claims, 6 Drawing Figures

IMMERSION SAMPLER FOR MOLTEN METAL

BACKGROUND OF THE INVENTION

Obtaining samples of molten metal for laboratory analysis has been a problem confronting metallurgists for many years. In recent years efforts have been made to obtain the sample by immersing a sample taking and forming device into the bath of molten metal. U.S. Pat. No. 3,455,164 issued to G. P. Boyle discloses one such sampling device in which the sampler body consisted of two sections of a shell molding made from resin coated sand and cemented together. The purpose for using the resin coated sand was to permit gas to escape through the body of the mold. As set forth in the patent, the shell molding technique includes the step of baking to harden to give the mold mechanical strength. One of the problems associated with the shell molding step of baking to provide mechanical strength is that as the baking time and temperature are increased to improve the strength of the mold, the material loses its porosity and characteristic of permitting gas to pass therethrough. The baking step must then be at best a compromise situation between strength and porosity.

It has also been found that the mold constructed by the shell molding technique generates or releases gas when subjected to the temperature of molten iron or steel. Not only does this gas increase the total volume of gas to be vented by adding to the gases trapped in the mold cavity and those released from the metal as it cools, but it represents a possible source of contamination of the metal sample.

Another approach to a sampler design is disclosed in U.S. Pat. No. 3,557,624 issued to W. J. Collins showing a pin sampling device using a fibrous material such as steel wool to provide a venting of entrapped gases into a chamber of limited volume. Additionally the sampler utilizes a plurality of metallic cups to provide entrance passages for the sample. Because of the limited volume of the venting chamber there exists the possibility that there is not sufficient venting capacity. This possibility is particularly great where the sampler is used to obtain samples from a bath that has a high degree of superheat and thus liberates large quantities of gases as the metal cools. Additionally there exists in this design the possibility of contamination of the sample when the sample contacts the steel wool.

Applicant has discovered that the devices taught in the prior art have failed to provide a device that has sufficient dependability that it can be used under the wide variation of conditions existing throughout the molten metal industry. While the devices of the prior art might function properly with certain bath conditions, the same device might due to differences in temperatures and molten metal composition not perform satisfactorily when used with other molten metal baths. Furthermore, the devices of the prior art resulted in the possibility of contamination of the sample from the materials used to provide restricted venting.

SUMMARY OF THE INVENTION

In accordance with applicant's invention there is provided an improved, low cost, totally expendable immersion sampler device of the hydraulic fill type. The construction of the mold permits its use under widely varying conditions and permits the rapid obtainment of a spectrographic and a pin sample. It is also an object of applicant's invention to provide apparatus for measuring the temperature of a molten metal bath at the time that the device is immersed for obtaining the samples. The temperature sensing element is of the expendable immersion thermocouple type such as shown in U.S. Pat. No. 2,999,121 issued to H. G. Mead. There is also included in the temperature measuring features of this invention a modified thermocouple holding arrangement having the advantages of the expendable immersion thermocouple shown in U.S. Pat. No. 3,298,874 issued to R. E. Davies.

It is further an object of applicant's invention to provide a contamination-free venting arrangement having good mechanical strength and permitting the rapid escape of entrapped and released gas from the molten metal sample as it enters the sampling chamber or cavity and solidifies therein to permit the obtainment of a completely formed and usable sample. The monolithic chamber defining member together with the porous plug member is particularly useful in eliminating flash or fins from the edges of the sample created when split molds are used.

It is a still further object of applicant's invention to provide a molten metal sampler and temperature measuring device that because of its novel features is easy to manufacture and provides a reliability exceeding those of the prior art.

Applicant's invention may best be understood from the following written description taken together with reference to the various figures of drawing.

DESCRIPTION OF PREFERRED EMBODIMENTS

Figure 2:
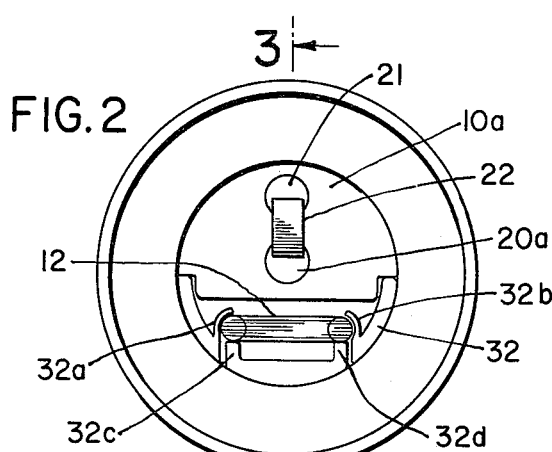
FIG. 2 is an end view of the sampling device.
Figure 1:
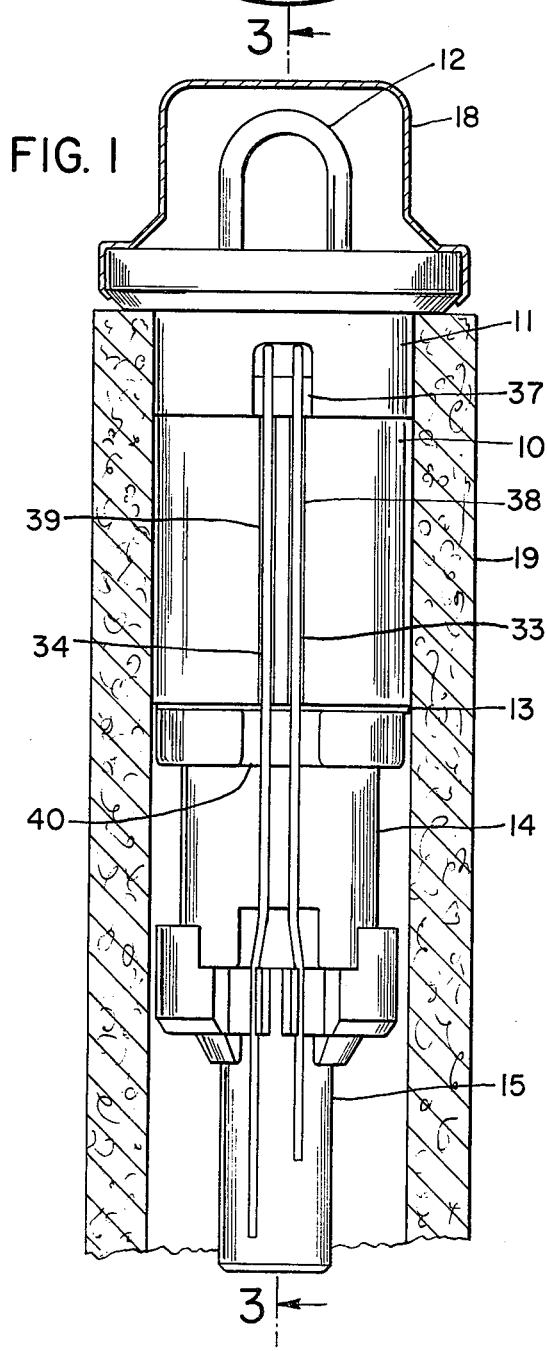
FIG. 1 is a side elevation, partly in section, of applicant's sampling device.

Referring to FIG. 1 there is shown an immersion molten metal sampler for obtaining a sample from a bath of molten material and the simultaneous measurement of the temperature of that bath. The sampler is composed of a monolithic cylindrical body member 10 having a substantially semi-cylindrical projection 10a (FIG. 2) at the front or immersion end of the body member 10. A ring member 11 is provided around the projection 10a for securing a bath temperature measuring element enclosed in a protective envelope 12. Attached to the other end of the monolithic cylindrical body member 10 by a suitable high temperature bonding refractory cement 13 such as Sauresan No. 1 manufactured by Sauresan Company is a porous ceramic plug 14 which in turn is cemented to a tail piece member 15.

In actual use the immersion sampler is provided with a heat destructible closure shown in section in FIG. 1 as cap 18. Also, the sampler device is in use provided with a holder or immersion assembly device comprising a tube of heat resistant material, such as cardboard or graphite, shown in section as a tube 19. As is well known to those skilled in the art, the cap 18 permits insertion of the device through the slag formation on the top of a molten metal bath before the cap melts to expose the openings of the sampling cavities or chambers and the temperature measuring element in the envelope 12 to the molten metal in the bath. The heat resistant tube 19 serves to protect the lead wires leading from the temperature measuring element to an appropriate indicating device and the electrical contacts associated therewith.

Figure 3:
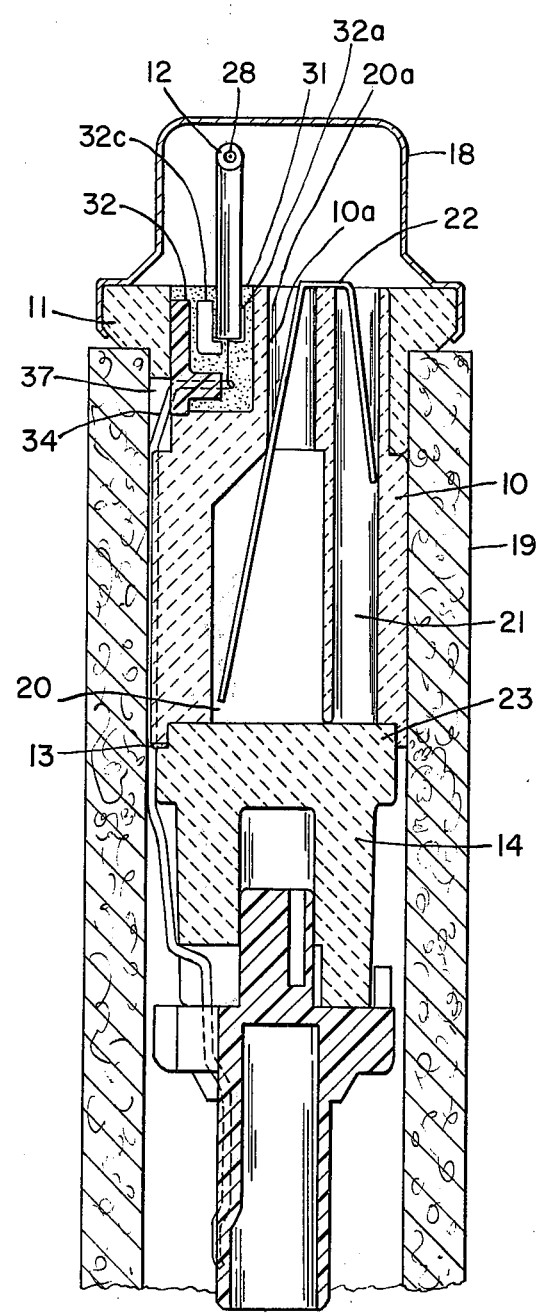
FIG. 3 is a sectional view taken along the line 3—3 of FIG. 2.

FIG. 3 shows a sectional view of the sampling device more clearly to disclose the features of applicant's invention. Within the monolithic cylindrical body member 10 there is shown a chamber 20 extending throughout the length of the body member 10. It will be noted that entrance 20a through projection 10a to the chamber 20 is of smaller dimension than the chamber itself. The shape of the chamber 20 is such as to provide a flat relatively rectangular solidified sample of the metal of the bath, which sample is particularly useful for spectrographic analysis to determine the composition of the bath. The body member 10 is made of a smooth surfaced, high density, gas impervious, ceramic material to produce a sample having a surface characteristic such that the sample requires little surface preparation prior to its use in the laboratory. A preferred ceramic for this body member 10 having the necessary characteristics is cordierite which is composed of alumina, magnesia and silica. This material is capable of withstanding temperatures as high as 3000°F. The body member is manufactured from cordierite by pouring the ceramic slip into a mold and firing the material.

The restricted entrance 20a together with the mass of the high density material of the monolithic body 10 serves rapidly to freeze the sample of molten metal to reduce the possibility of loss of sample from the opening 20a as the sampler device is removed from the molten metal bath. In addition to the chamber 20 for obtaining a rectangular shaped sample for spectrographic analysis there is also shown in the sampler of FIG. 3 a chamber 21 extending throughout the length of the body member 10. This chamber 21 is substantially a cylindrical chamber for the purpose of obtaining a pin sample used in metallurgical laboratories for combustion analysis for determining the present carbon and sulfur content of the molten metal in the bath.

In FIG. 3 there is additionally shown inserted within the chambers 20 and 21 a metal strip 22 of deoxidizing material. The strip 22 is made of aluminum which mixes with the entering steel sample to deoxidize it. As the quantity of molten metal entering the chamber 20 is obviously greater than that entering the chamber 21 the length of the strip 22 inserted into the chamber 20 is greater than the length of the strip inserted in chamber 21 to provide ample deoxidation of both samples.

It will be noted that the side walls of the body member 10 extend beyond the lower ends of the chambers 20 and 21 producing a shouldered cylindrical cavity 23 within the body member 10. As shown in FIG. 3, the plug 14 made of a porous ceramic such as cordierite includes a forward projection of reduced diameter which when the body members 10 and 14 are secured together by cement 13 projects into the cavity 23 for improved mechanical holding and to provide a porous, gas permeable end wall for the cavities 20 and 21. As previously described, the porous ceramic plug or body member 14 provides a venting means for gases trapped within the chambers 20 and 21 due to immersion in the molten metal and for gases liberated from the samples of molten metal as they cool in the chambers 20 and 21. As the porous ceramic is gaseously inert at the temperatures of the molten metal there is no problem of contaminating the samples in chambers 20 and 21 by gases that might be generated by the plug 14. Also inasmuch as the porous ceramic liberates no gases the volume of gas that must be vented from the sampler is less than it would be if the material of the venting means liberated gases when exposed to molten metal temperatures. It is to be noted that the cylindrical body of plug 14 is of smaller diameter than the inside diameter of the heat resistant tube 19. This dimensional difference provides a passageway for vented gases rapidly to escape from the outer surface of the plug 14 and flow to atmosphere through the inside of heat resistant tube 19.

Figure 6:
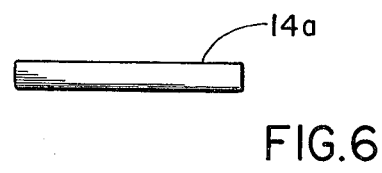
FIG. 6 is a side elevation of a cylindrical porous plug member.

If the sampling device is to be employed for obtaining only a spectrographic sample and a pin sample, the porous ceramic plug may take the form of a flat disk 14a (FIG. 6) having dimensions substantially the same as the dimensions of the cavity 23. However, if an addition to obtaining the samples it is also desired to obtain the temperature of the molten metal bath, then the plug 14 may take the shape substantially as shown in FIGS. 1 and 3 in order that the lead wires from the thermocouple element used to measure the temperature and the contacts with which the lead wires connect are sufficiently removed from the molten metal bath so that repeated immersions will not damage the mating contact structure.

Figure 5:
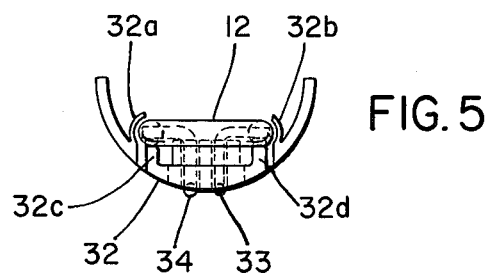
FIG. 5 is an end view of the thermocouple holding structure of FIG. 4.
Figure 4:
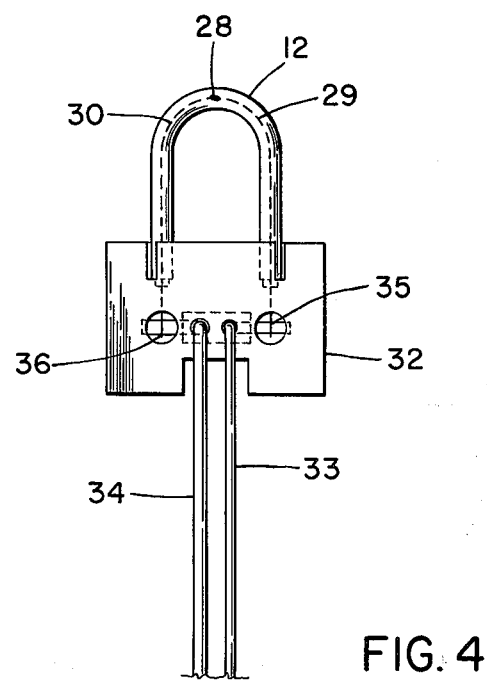
FIG. 4 is a side elevation view showing the novel thermocouple holding structure of applicant's invention.

When it is desired to measure the temperature of the molten metal bath the design of the molten metal sampling device lends itself uniquely to the addition of an expendable immersion thermocouple. FIG. 4 shows a thermocouple junction 28 between two dissimilar metals 29 and 30 to form the hot junction of a thermocouple for the thermoelectric determination of the temperature of the molten metal bath. When the molten metal is steel the thermocouple wire 29 may be platinum and the thermocouple wire 30 may be platinum, 10% rhodium. As is well known in the expendable immersion thermocouple art, this thermocouple junction is protected by a thin-walled quartz or fused silica tube 12 to provide electrical insulation and good heat transmission. As shown in FIGS. 4 and 5, the tube 12 is held in a thermocouple securing member 32 of substantially semi-circular shape and having resilient protrusions 32a and 32b which due to their resiliency firmly secure the tube 12 against projections 32c and 32d of the thermocouple securing member 32. Preferably the thermocouple securing member 32 may be molded of a resilient plastic such as polypropylene.

Attached to and also secured to the member 32 are a pair of thermocouple lead wires 33 and 34. These thermocouple lead wires are welded to the thermocouple wires as shown in FIG. 4 at 35 and 36 respectively. The other ends of the lead wires 33 and 34 extend as shown in FIG. 1 to the tail piece member 15 wherein they provide a contact structure in a manner well known to those skilled in the art for providing a nondirectional coupling with ring type contact elements connected to temperature measuring and/or recording means (not shown).

Returning to FIG. 3 it will be noted that the thermocouple junction 28 in protective envelope 12 and the thermocouple securing member 32 have been shown secured in position adjacent the projection 10a of cylindrical body member 10. As shown more clearly in FIG. 2, the projection 10a of body member 10 has a substantially semi-cylindrical form of diameter less than the diameter of the main part of the body 10. The semi-circular shape of the thermocouple securing member 32 shown in FIG. 5 is approximately the same radius as the cylindrical wall of the projection 10a and of such arcuate length that when the thermocouple securing member 32 is positioned adjacent to the projection 10a of body member 10 the two combine to produce a substantially complete cylindrical surface.

In order to secure the member 32 in proper relation to the projection 10a the ring member 11 is placed in encircling relationship about the projection 10a and the member 32. The ring member 10 is preferably constructed of the same ceramic material as body member 10 and has an inner diameter to mate with that of the cylindrical surface formed by projection 10a and member 32.

The open space surrounding the thermocouple securing member 32 and within the ring member 11 is then filled with an appropriate refractory cement 31 maintaining the parts in their assembled position. Not only does ring member 11 serve to physically retain the parts in their proper spatial relationship but it also serves to shield the junction between the thermocouple wires and the thermocouple lead wires from the temperature of the molten metal bath during the time that the thermocouple is responding to the temperature of the molten metal is to provide an indication of the temperature of the bath.

As shown in FIG. 1 the thermocouple lead wires 22 and 34 pass through notch 37 in ring 11 and extend along the outer surface of body member 10. In order to facilitate the insertion of the sampler into the heat resistant tube 19 the cylindrical surface of body member 10 includes longitudinal grooves 38 and 39 to permit the lead wires 33 and 34 to be recessed below the surface of body member 10. Notch 40 in the side wall of the porous ceramic member 14 also serves a similar function. The thermocouple lead wires 33 and 34 terminate in curved contact surfaces in the reduced diameter part of tail piece 15 to provide, in manner well known to those skilled in the art, a connection to appropriate mating contact surfaces connected to a temperature measuring instrument.

It should be understood that the invention is not limited to the specific arrangements shown herein and that changes and modifications may be made therein and additional sensing devices may be included therewith to provide, for example, for the measurement of dissolved oxygen in the bath and/or bath carbon by thermal arrests as the sample cools.

What is claimed is:

1. A multi-body, molten-metal, end-fill sampler for immersion into a bath of molten metal for obtaining a solidified sample of said metal for laboratory analysis to determine the composition of the molten metal comprising a first substantially cylindrical monolithic body member constructed of a smooth surfaced, high density, gas impervious, ceramic material having a chamber extending the length of said first body member with at least a thick walled entrance passage for collection of a sample of the molten metal and the rapid cooling of said sample to produce quick freezing of said sample;

a second substantially cylindrical body member constructed of a gas permeable, liquid impermeable ceramic material having a high gas transfer rate capable of allowing gas to pass readily therethrough and blocking passage of said molten metal and constructed of a material that is gaseous inert at the temperature of said molten metal and has a coefficient of thermal expansion substantially the same as the material of said first body member, adhesive material means for joining said first and second body member means together in a gas sealed joint whereby said second body member means serves as the sole gas venting means for said chamber in said first body means; and insertion means for immersion of said sampler below the level of molten metal to be sampled.

2. A sampler according to claim 1 in which said first body member has extending side walls to produce a cylindrical cavity in one end to receive said second body member.

3. A sampler according to claim 2 in which said second body member is a flat cylinder having a diameter substantially the same as the diameter of said cylindrical cavity and a thickness substantially corresponding with the depth of said cavity.

4. A multi-body, molten-metal, end-fill sampler for immersion into a bath of molten metal for obtaining a solidified sample of said metal for laboratory analysis to determine the composition of the molten metal comprising a first substantially cylindrical monolithic body member constructed of a smooth surfaced, high density, gas impervious, ceramic material having a chamber extending the length of said first body member, said first body member having a semi-cylindrical projection with a surface defining a semi-circular shape of radius less than the radius of said body member, an entrance passage to the said chamber extending through said projection, a second cylindrical body member constructed of a gas permeable liquid impermeable ceramic material having a high gas transfer rate capable of allowing gas to pass readily therethrough and blocking passage of said molten metal that is gaseous inert at the temperature of said molten metal; said ceramic material of said second body member having a coefficient of thermal expansion substantially the same as the material of said first body member, adhesive material means for joining said first and second body member means together in a gas sealed joint whereby said second body member means serves as the sole non-contaminating, gas-venting means for said chamber in said first body member, and insertion means for immersion of said sampler below the level of molten metal to be sampled.

5. A sampler according to claim 4 in which said chamber is of substantially rectangular shape.

6. A sampler according to claim 5 additionally including a cylindrical hole of small diameter extending throughout said first body member and said projection to provide a pin sample.

7. A sampler according to claim 5 including a quantity of a deoxidizing material in said entrance passage.

8. A sampler according to claim 5 including a closure of heat destructible material covering the entrance to said chamber.

9. A sampler according to claim 5 wherein said immersion means comprises a tube of heat resistant material with said first and second body members supported in one end thereof.

10. A sampler according to claim 4 additionally including a thermocouple and means for supporting said thermocouple adjacent said projection with the junction of said thermocouple extending beyond the outer face of said projection.

11. A sampler according to claim 10 in which said means for supporting said thermocouple includes a semi-cylindrical member of radius corresponding to the radius of said projection and having resilient means integral therewith for securing said thermocouple, and
- a ring means having an inner radius corresponding to the radius of said projection and said semi-cylindrical member and an outer diameter corresponding to the diameter of said first body member encircling said thermocouple supporting means and said projection.

12. A sampler according to claim 11 additionally including thermocouple lead wires secured to said thermocouple supporting means for connection with said thermocouple and in which said ring member includes a passageway in a side wall for passage of said lead wires along the outer surface of said first body member to provide electrical contacts for connection of said thermocouple to a temperature measuring circuit.

13. A sampler according to claim 12 in which the void within said ring between said projection and said thermocouple supporting means is filled with cement.

14. A sampler according to claim 13 including a tail piece of resilient material cemented to the end of said second body member and in which the surfaces of said first and second body members are reduced in cross section to permit the passage of said lead wires to said tail piece and said lead wires are supported by said tail piece to form said contacts.

* * * * *